United States Patent
Baltruschat et al.

[11] Patent Number: 5,985,796
[45] Date of Patent: Nov. 16, 1999

[54] HERBICIDAL MIXTURES

[75] Inventors: Helmut Siegfried Baltruschat, Schweppenhausen; Astrid Brandt, Mainz, both of Germany

[73] Assignee: American Cyanamid Company, Madison, N.J.

[21] Appl. No.: 09/010,868

[22] Filed: Jan. 22, 1998

[51] Int. Cl.$^6$ .................. A01N 43/40; A01N 43/54; A01N 43/56; A01N 43/70
[52] U.S. Cl. .................................. 504/130; 504/139
[58] Field of Search ...................... 504/130, 139

[56] References Cited

U.S. PATENT DOCUMENTS 5,840,654  11/1998  Kleemann ........................ 504/251

FOREIGN PATENT DOCUMENTS

WO 94/22833  10/1994  WIPO .................. C07D 213/69
WO 94/07368  4/1996  WIPO .................. A01N 43/40

OTHER PUBLICATIONS

U.S. application Ser. No. 08/688,473, Baltruschat, filed Jul. 30, 1996.

*Primary Examiner*—S. Mark Clardy
*Attorney, Agent, or Firm*—Joseph M. Mazzarese

[57] ABSTRACT

A herbicidal composition comprising a herbicidally acceptable carrier and/or surface active agent and, as active ingredient, a synergistically effective amount of (1) at least one 2,6-disubstituted pyridine of formula I

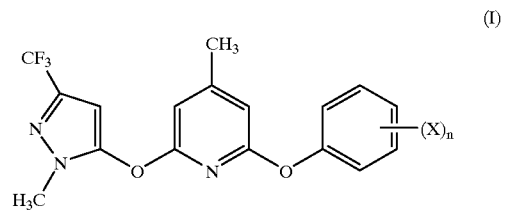

(I)

in which
   x independently represents a halogen atom or a haloalkyl group; and
   n is an integer of 1, 2 or 3; and
(2) at least one additional herbicidal compound, which is active against broad-leaved weeds and/or annual grasses; which provides a synergistic effect against a broad spectrum of weed species, e.g., in cereal crops, and a method for controlling weeds by applying a synergistically effective amount of a compound (1) and a compound (2) to a locus.

11 Claims, No Drawings

HERBICIDAL MIXTURES

BACKGROUND OF THE INVENTION

The present invention relates to an improvement in the efficacy of herbicidal 2,6-substituted pyridines by combination with a selected second herbicidal compound.

The herbicidal 2,6-disubstituted pyridines to be used according to the present invention are a group of compounds, disclosed in International Application WO 94/22833, which display excellent herbicidal performance, in particular against broad-leaved weeds in cereal crops. However, the 2,6-disubstituted pyridines, when used as the sole active ingredient, do not always achieve effective control of the full spectrum of weed species encountered in commercial agronomic applications, in conjunction with reliable selectivity for the crop species. Such gaps in the spectrum of control can be overcome by co-treatment with another herbicide known to be effective against the relevant weed species. The combined use of herbicidal pyridines and other herbicides has been described in International Patent Application WO 94/07368.

Surprisingly, it has now been found, that the combined herbicidal activity of certain 2,6-disubstituted pyridines with various other herbicides against many broad-leaved weeds and annual grasses is much greater than expected when applied pre- or post-emergence and that this activity cannot be ascribed to an additive effect, but to a remarkable degree of synergism on many broad-leaved weed species and annual grasses, for example on Setaria viridis, Alopecurus myosuroides, Poa annua, Stellaria media, Lamium purpureum, Galium aparine, Veronica hederaefolia, Papaver rhoeas or Matricaria inodora. These combinations show a much higher level of activity than predicted from that of the individual compounds, which also enables a greater selectivity for the crop species.

A mixture of herbicides shows synergistic effect if the herbicidal activity of the mixture is larger than the sum of activities of the separately applied compounds. The expected herbicidal activity for a given mixture of two herbicides can be calculated as follows (See Colby, S. R., "Calculating synergistic and antagonistic response of herbicide combinations", Weeds 15, pp 20–22 (1967):

$$WE = X + \frac{Y \times (100 - X)}{100}$$

wherein

X is the percentage of growth inhibition upon treatment with a herbicide 1 at a dose of p kg/ha compared with an untreated control (X=0%)

Y is the percentage of growth inhibition treatment with a herbicide 2 at a dose of q kg/ha compared with an untreated control WE is the herbicidal effect to be expected upon treatment (% of growth inhibition compared with untreated control) with a combination of herbicide 1 and 2 at a dose of p+q g/ha, respectively.

If the actual weed control (W) exceeds the expected (calculated) eed control (WE), the mixture displays a synergistic effect.

SUMMARY OF THE INVENTION

The present invention includes a herbicidal composition comprising, as active ingredient, a synergistically effective amount of at least one 2,6-disubstituted 4-methyl pyridine of formula I

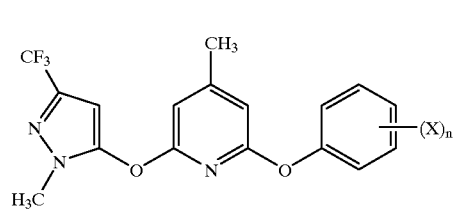

in which

X represents independently a halogen atom or a haloalkyl group; and n represents an integer of 1, 2 or 3; and (1) at least one additional herbicidal compound, which is active against broad-leaved weeds and/or annual grasses.

The present invention also includes a method for controlling undesirable plant species comprising application of at least one compound of formula I and at least one additional herbicidal compound, as defined above. In the method of this invention, these compounds may be applied separately or together, in herbicidally effective amounts.

DETAILED DESCRIPTION OF THE PREFERRED EMBODIMENTS

Preferred compounds for use as 2,6-disubstituted 4-methyl pyridines according to the invention are the compounds of formula I, wherein X represents a fluoro atom and n is 1 or 2, in particular 2-(3,4-difluorophenoxy)-4-methyl-6-(1-methyl-3-trifluoromethylpyrazol-5-yl)-pyridine (Compound A).

The additional compounds having herbicidal activities against broad-leaved weeds and/or annual grasses are preferably selected from a) urea-type herbicide, such as chlortoluron, isoproturon, linuron or neburon, b) a triazine-type herbicide, such as atrazine, cyanazine or simazine, c) a hydroxybenzonitrile herbicide, such as bromoxynil or ioxynil, d) an aryloxyalkanoic acid herbicide, such as dichlorprop, 4-chloro-2-methylphenoxyacetic acid ("MCPA") or mecoprop, e) a dinitroaniline herbicide, such as pendimethalin, f) a sulfonylurea herbicide, such as amidosulfuron, g) a pyridazine herbicide, such as pyridate, h) a fluorene carboxylic acid herbicide, such as flurenol, i) a pyridyloxyacetic acid herbicide, such as fluroxypyr, j) a fenoxyfenoxypropionie acid herbicide, such as fenoxaprop, and k) an oxyacetamide herbicide, such as fluthiamide.

The pattern of persistence of the 2,6-substituted pyridine (abbreviated herein as "BAP") is such that the combined treatment according to the present invention can be attained either by the application of a prepared mixture as defined above, or by time separated application of separate formulations. Hence, in another preferred embodiment, the present invention provides a method for controlling the growth of weeds at a cereal crop locus which comprises applying to the locus a BAP as defined above and a second component which is selected from those listed above as types (a)–(k).

The treatment according to the invention may be used to control a broad spectrum of weed species in cereal crops, e.g., in wheat, barley, rice and maize, by pre- or post-emergence treatment, including both early and late post-emergence The combined use described above offers both foliar and residual activity.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. It will be appreciated that application according to the method may be from pre- to post-weed emergence, and from pre-crop emergence to post-crop emergence. By the term "foliar activity" is meant herbicidal activity obtained by application to the aerial or exposed portions of the weeds which have emerged above the surface of the soil. By the term "residual activity" is meant herbicidal activity obtained some time after application to the soil whereby seedlings present at the time of application or which germinate subsequent to application are controlled.

Weeds that may be controlled by the practice of the present invention include:

| | | |
|---|---|---|
| Veronica persica | Veronica hederaefolia | Stellaria media |
| Lamium purpureum | Lamium amplexicaule | Aphanes arvensis |
| Galium aparine | Alopecurus myosuroides | Matricaria inodora |
| Matricaria matricoides | Anthemis arvensis | Papaver rhoeas |
| Poa annua | Apera spica-venti | Phalaris paradoxa |
| Phalaris minor | Avena fatua | Lolium perenne |
| Bromus sterilis | Poa trivialis | Spergula arvensis |
| Cerastes holosteoides | Arenaria seryllifolia | Silene vulgaris |
| Legousia hybrida | Geranium dissectum | Montia perfoliata |
| Myosotis arvensis | Chenopodium album | Polygonum aviculare |
| Polygonum lapathifolium | Polygonum convolvulus | Galeopsis tetrahit |
| Chrysantemum segetum | Centaurea cyanus | Viola arvensis |
| Senecia vulgaris | Cirsium arvense | Fumaria officinalis |
| Raphanus raphanistrum | Agrostis stolonifera | Atriplex patula |
| Capsella bursa-pastoris | Thlaspi arvense | Portulaca oleracea |
| Setaria viridis | Eleusine indica | Euphorbia helioscopia |

The application rate of the compound of formula I is usually in the range of 5 to 500 grams of active ingredient (g a.i.) per hectare, with rates between 7.5–100 g a.i./ha often achieving satisfactory control and selectivity. The optimal rate for a specific application will depend on the crop(s) under cultivation and the predominant species of infesting weed, and readily may be determined by established biological tests known to those skilled in the art.

The selection of the herbicidally active compound of types (a)–(k) will likewise be dependent on the crop/weed species to be treated, and will be readily identifiable by those skilled in this area. The application rate of this active component is determined primarily by the chemical type of the component, since the intrinsic activity of different types of herbicide varies widely. For example, the activity of a triazine herbicide, such as cyanazine or simazine, can be almost tenfold greater than that of an urea herbicide such as chlortoluron or isoproturon. In general, the preferred application rate of this active ingredient is in the range of 100 to 2500 g a.i./ha, preferably 100–1500 g a.i./ha, for an urea herbicide; in the range of 7.5 to 100 g/ha, for a sulfonylurea herbicide; in the range of 75–400 g/ha for a hydroxybenzonitrile herbicide; in the range of 100–1200 g a.i./ha, for an aryloxyalkanoic acid herbicide; in the range of 250 to 2500 g/ha, for a dinitroaniline herbicide such as pendimethalin; in the range of 40 to 200 g/ha, for a pyridyloxyacetic acid herbicide such as fluroxypyr; in the range of 25 to 250 g/ha, for a fenoxyfenoxypropion acid herbicide; and in the range of 25 to 500 g/ha, for an oxyacetamide herbicide. The optimal rate for the chosen non-BAP component will, however, depend on the crop(s) under cultivation and the level of weed infestation, and can readily be determined by established biological tests. Naturally, with such a wide variation in application rate for the non-BAP component, the ratio of a BAP to a non-BAP component in the present invention will be determinded predominantly by the choice of the non-BAP component. The ratio (by weight) of the 2,6-disubstituted pyridine to the additional herbicidal compound is, as a rule, from 10:1 to 1:200, preferably from 2:1 to 1:150, in particular from 1:1 to 1:80. The preferred ratio BAP: non-BAP may vary, e.g., from about 1:1 (Bromoxynil) to about 1:64 (Isoproturon).

The active compounds can be used in the form of a mixture of separate formulations, typically mixed with water prior to application (tank-mixtures), or as separate formulations applied individually within a certain time interval. Both active compounds can also be formulated together in a suitable ratio according to the present invention, together with usual carriers and/or additives known in the art.

Accordingly, the invention further provides a herbicidal composition which comprises as active ingredient, a synergistically effective amount of at least one compound of formula I as defined above, and at least one compound selected from types (a)–(k) and one or more carriers. A method of making such a composition is also provided which comprises bringing the mixture of the compound of formula I and the compound selected from types (a)–(k) as defined above into association with the carrier(s). It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredients.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. SOLVESSO® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pregranulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and retention enhancers (stickers), and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
|---|---|---|
| Active Ingredient | Compound A + Isoproturon (1:8) | 30% (w/v) |
| Emulsifier(s) | Atlox ® 4856 B/Atlox ® 4858 B[1] (mixture containing calcium alkyl aryl sulfonate, fatty alcohol ethoxylates and light aromatics/ mixture containing calcium alkyl aryl sulfonate, fatty alcohol ethoxylates and light aromatics) | 5% (w/v) |
| Solvent | Shellsol ® A[2] (mixture of $C_9$–$C_{10}$ aromatic hydrocarbons) | to 1000 ml |
| Suspension Concentrate (SC) | | |
| Active Ingredient | Compound A + Chlortoluron (1:16) | 50% (w/v) |
| Dispersing agent | Soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |
| Wettable Powder (WP) | | |
| Active Ingredient | Compound A + Fluthiamide (1:2) | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates | 3% (w/w) |
| Carrier/Filler | Kaolin | 35% (w/w) |
| Water Dispersible Granules (WG) | | |
| Active Ingredient | Compound A + Cyanazine (1:4) | 50% (w/w) |
| Dispersing/ Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |

-continued

| Carrier/Filler | Kaolin | 35% (w/w) |
|---|---|---|

[1]commercially available from ICI Surfactants
[2]commercially available from Deutsche Shell AG
[3]commercially available from Rhône-Poulenc
[4]commercially available from Kelco Co.
[5]commercially available from Zeneca
[6]commercially available from Witco
[7]commercially available from International Speciality Products The compositions of this invention can also comprise other compounds having biological activity, e.g. compounds having similar or complementary pesticidal activity or compounds having plant growth regulating, fungicidal or insecticidal activity. These mixtures of pesticides can have a broader spectrum of activity than the synergistic composition according to this invention alone.

The following examples illustrate specific embodiments of the present invention; however, the invention is not limited to the embodiments so illustrated, but includes the entire scope of the appended claims.

EXAMPLES

General Method

The trials are carried out under greenhouse conditions in pre- and post-emergence applications. The plant seeds are sown in pots containing a loamy sand soil (0.5 l). The herbicides are applied as single treatments, or in a combination comprising a compound of formula I and compound selected from group (2) as defined above, before or after emergence of weeds and crop. The herbicidal performance is assessed as percent damage in comparison to the untreated control plants. The assessment is done 21 days after the treatment. Wheat and barley are treated at the 3–4 leaf stage, the broad-leaf weeds at the 2–4 leaf stage and annual grasses at the 2–3 leaf stage.

For the compound of formula I Compound A is employed. The other component selected from group (2) is identified in each example by its common name with application rates (and hence component ratios) chosen to be appropriate to the established activity level of that component.

Fluthiamide is the proposed common name of N-(fluorophenyl)-N-(1-methylethyl)-2-[[5-(trifluoromethyl)-1,3,4-thiadiazol-2-yl]oxy]acetamide, which is disclosed for example in the German patent application DE 38 21 600.

The following abbreviations have been used in the tables:
WE: expected response by means of the Colby formula;
W: observed response.

The results of these experiments are tabulated as Examples 1 to 5 wherein all the results from a chosen component of group (2) are collected under the same Example number, different dosage rates/test species being recorded in the examples. From these results, it is clear that synergism exists between the compounds of formula I and the compounds selected from group (2). Crop tolerance (wheat and barley) is excellent in all treatments.

Example 1 A

Herbicidal performance of the mixture Compound A+Isoproturon (60 g a.i./ha+120 g a.i./ha=mixture 1:2) against grasses in post-emergence application

| weed species | Compound A 60 g a.i./ha | Isoproturon 120 g a.i./ha | Compound A + Isoproturon 60 + 120 g a.i./ha | |
|---|---|---|---|---|
| | % control | | WE | W |
| Alopecurus myosuroides | 87 | 57 | 94 | 100 |
| Lolium perenne | 37 | 32 | 57 | 91 |
| Setaria viridis | 67 | 45 | 82 | 94 |

Expected control of Alopecurus myosuroides, Lolium perenne and Setaria viridis was 94, 57 and 82 respectively, clearly demonstrating that the combination was synergistic.

Example 1 B

Herbicidal performance of the mixture Compound A+Isoproturon (30 g a.i./ha+120 g a.i./ha=mixture 1:4) against grasses in post-emergence application

| weed species | Compound A 30 g a.i./ha | Isoproturon 120 g a.i./ha | Compound A + Isoproturon 30 + 120 g a.i./ha | |
|---|---|---|---|---|
| | % control | | WE | W |
| Alopecurus myosuroides | 82 | 57 | 92 | 100 |
| Lolium perenne | 22 | 32 | 47 | 94 |
| Setaria viridis | 50 | 45 | 73 | 86 |

Expected control of Alopecurus myosuroides, Lolium perenne and Setaria viridis was 92, 47 and 73 respectively, clearly demonstrating that the combination was synergistic.

Example 1 C

Herbicidal performance of the mixture Compound A+Isoproturon (60 g a.i./ha+240 g a.i./ha=mixture 1:4) against Lolium perenne in post-emergence application

| weed species | Compound A 60 g a.i./ha | Isoproturon 240 g a.i./ha | Compound A + Isoproturon 60 + 240 g a.i./ha | |
|---|---|---|---|---|
| | % control | | WE | W |
| Lolium perenne | 37 | 67 | 79 | 100 |

Expected control of Lolium perenne was 79, clearly demonstrating that the combination was synergistic.

Example 1 D

Herbicidal performance of the mixture Compound A+Isoproturon (30 g a.i./ha+240 g a.i./ha=mixture 1:8) against Lolium perenne in post-emergence application

| weed species | Compound A 30 g a.i./ha | Isoproturon 240 g a.i./ha | Compound A + Isoproturon 30 + 240 g a.i./ha | |
|---|---|---|---|---|
| Alopecurus myosuroides | 82 | 86 | 97 | 100 |

-continued

| weed species | Compound A 30 g a.i./ha | Isoproturon 240 g a.i./ha | Compound A + Isoproturon 30 + 240 g a.i./ha | |
|---|---|---|---|---|
| Lolium perenne | 22 | 67 | 74 | 96 |

Expected control of Lolium perenne was 74, clearly demonstrating that the combination was synergistic.

Example 1 E

Herbicidal performance of the mixture Compound A+Isoproturon (15 g a.i./ha+120 g a.i./ha mixture 1:8) against Stellaria media in pre-emergence application

| | Compound A 15 g a.i./ha | Isoproturon 120 g a.i./ha | Compound A + Isoproturon 15 + 120 g a.i./ha | |
|---|---|---|---|---|
| weed species | % control | | WE | W |
| Stellaria media | 35 | 0 | 35 | 88 |

Expected control of Stellaria media was 35, clearly demonstrating that the combination was synergistic.

Example 1 F

Herbicidal performance of the mixture Compound A+Isoproturon (30 g a.i./ha+240 g a.i./ha=mixture 1:8) against grasses in pre-emergence application

| | Compound A 30 g a.i./ha | Isoproturon 240 g a.i./ha | Compound A + Isoproturon 30 + 240 g a.i./ha | |
|---|---|---|---|---|
| weed species | % control | | WE | W |
| Alopecurus myosuroides | 35 | 50 | 68 | 87 |
| Setaria viridis | 82 | 15 | 85 | 100 |

Expected control of Alopecurus myosuroides and Setaria viridis was 68 and 85 respectively, clearly demonstrating that the combination was synergistic.

Example 1 G

Herbicidal performance of the mixture Compound A+Isoproturon (7,5 g a.i./ha+120 g a.i./ha=mixture 1:16) against broad-leaved weeds in pre-emergence application

| | Compound A 7.5 g a.i./ha | Isoproturon 120 g a.i./ha | Compound A + Isoproturon 7.5 + 120 g a.i./ha | |
|---|---|---|---|---|
| weed species | % control | | WE | W |
| Stellaria media | 5 | 0 | 5 | 85 |
| Veronica persica | 87 | 0 | 87 | 96 |
| Lamium purpureum | 57 | 0 | 57 | 98 |

Expected control of Stellaria media, Veronica persica and Lamium purpureum was 5, 87 and 57 respectively, clearly demonstrating that the combination was synergistic.

Example 1 H

Herbicidal performance of the mixture Compound A+Isoproturon (15 g a.i./ha+240 g a.i./ha=mixture 1:16) against grasses and broad-leaved weeds in pre-emergence application

| | Compound A 15 g a.i./ha | Isoproturon 240 g a.i./ha | Compound A + Isoproturon 15 + 240 g a.i./ha | |
|---|---|---|---|---|
| weed species | % control | | WE | W |
| Alopecurus myosuroides | 5 | 50 | 53 | 83 |
| Setaria viridis | 35 | 15 | 45 | 67 |
| Stellaria media | 35 | 0 | 35 | 92 |

Expected control of Alopecurus myosuroides, Setaria viridis and Stellaria media was 53, 45 and 35 respectively, clearly demonstrating that the combination was synergistic.

Example 1 I

Herbicidal performance of the mixture Compound A+Isoproturon (7,5 g a.i./ha +240 g a.i./ha=mixture 1:32) against broad-leaved weeds in pre-emergence application

| | Compound A 7.5 g a.i./ha | Isoproturon 240 g a.i./ha | Compound A + Isoproturon 7.5 + 240 g a.i./ha | |
|---|---|---|---|---|
| weed species | % control | | WE | W |
| Stellaria media | 5 | 0 | 5 | 77 |
| Veronica persica | 87 | 0 | 87 | 100 |
| Lamium purpureum | 57 | 0 | 57 | 90 |

Expected control of Stellaria media, Veronica persica and Lamium purpureum was 5, 87 and 57 respectively, clearly demonstrating that the combination was synergistic.

Example 2 A

Herbicidal performance of the mixture Compound A+Chlortoluron (15 g a.i./ha+240 g a.i./ha=mixture 1:16) against Alopecurus myosuroides in pre-emergence application

| | Compound A 15 g a.i./ha | Chlortoluron 240 g a.i./ha | Compound A + Chlortoluron 15 + 240 g a.i./ha | |
|---|---|---|---|---|
| weed species | % control | | WE | W |
| Alopecurus myosuroides | 45 | 10 | 51 | 80 |

Expected control of Alopecurus myosuroides was 51, clearly demonstrating that the combination was synergistic.

Example 2 B

Herbicidal performance of the mixture Compound A+Chlortoluron (15 g a.i./ha+480 g a.i./ha=mixture 1:32) against Alopecurus myosuroides in pre-emergence application

|  | Compound A 15 g a.i./ha | Chlortoluron 480 g a.i./ha | Compound A + Chlortoluron 15 + 480 g a.i./ha | |
|---|---|---|---|---|
| weed species | % control | | WE | W |
| Alopecurus myosuroides | 45 | 45 | 70 | 88 |

Expected control of Alopecurus myosuroides was 70, clearly demonstrating that the combination was synergistic.

Example 2 C

Herbicidal performance of the mixture Compound A+Chlortoluron (60 g a.i./ha+960 g a.i./ha=mixture 1:16) against Lolium perenne in post-emergence application

|  | Compound A 60 g a.i./ha | Chlortoluron 960 g a.i./ha | Compound A + Chlortoluron 60 + 960 g a.i./ha | |
|---|---|---|---|---|
| weed species | % control | | WE | W |
| Lolium perenne | 37 | 37 | 60 | 89 |

Expected control of Lolium perenne was 60, clearly demonstrating that the combination was synergistic.

Example 3 A

Herbicidal performance of the mixture Compound A+Fluthiamide (30 g a.i./ha+30 g a.i./ha=mixture 1:1) against Alopecurus myosuroides and Galium aparine in pre-emergence application

|  | Compound A 30 g a.i./ha | Fluthiamide 30 g a.i./ha | Compound A + Fluthiamide 30 + 30 g a.i./ha | |
|---|---|---|---|---|
| weed species | % control | | WE | W |
| Alopecurus myosuroides | 67 | 65 | 88 | 94 |
| Galium aparine | 42 | 37 | 63 | 93 |

Expected control of Alopecurus myosuroides and Galium aparine was 88 and 63 respectively, clearly demonstrating that the combination was synergistic.

Example 3 B

Herbicidal performance of the mixture Compound A+Fluthiamide (15 g a.i./ha+30 g a.i./ha=mixture 1:2) against Alopecurus myosuroides in pre-emergence application

|  | Compound A 15 g a.i./ha | Fluthiamide 30 g a.i./ha | Compound A + Fluthiamide 15 + 30 g a.i./ha | |
|---|---|---|---|---|
| weed species | % control | | WE | W |
| Alopecurus myosuroides | 30 | 65 | 76 | 94 |

Expected control of Alopecurus myosuroides was 76, clearly demonstrating that the combination was synergistic.

Example 3 C

Herbicidal performance of the mixture Compound A+Fluthiamide (7,5 g a.i./ha+30 g a.i./ha=mixture 1:4) against Alopecurus myosuroides and broad-leaved weeds in pre-emergence application

|  | Compound A 7.5 g a.i./ha | Fluthiamide 30 g a.i./ha | Compound A + Fluthiamide 7.5 + 30 g a.i./ha | |
|---|---|---|---|---|
| weed species | % control | | WE | W |
| Alopecurus myosuroides | 25 | 65 | 74 | 96 |
| Lamium purpureum | 82 | 5 | 83 | 100 |
| Veronica persica | 50 | 25 | 63 | 95 |

Expected control of Alopecurus myosuroides, Lamium purpureum and Veronica persica was 74, 83 and 63 respectively, clearly demonstrating that the combination was synergistic.

Example 4 A

Herbicidal performance of the mixture Compound A+Cyanazine (60 g a.i./ha+60 g a.i./ha=mixture 1:1) against grasses in post-emergence application

|  | Compound A 60 g a.i./ha | Cyanazine 60 g a.i./ha | Compound A + Cyanazine 60 + 60 g a.i./ha | |
|---|---|---|---|---|
| weed species | % control | | WE | W |
| Alopecurus myosuroides | 90 | 10 | 91 | 100 |
| Lolium perenne | 47 | 22 | 59 | 83 |
| Setaria viridis | 70 | 55 | 87 | 95 |

Expected control of Alopecurus myosuroides, Lolium perenne and Setaria viridis was 91, 59 and 87 respectively, clearly demonstrating that the combination was synergistic.

Example 4 B

Herbicidal performance of the mixture Compound A+Cyanazine (30 g a.i./ha+60 g a.i./ha=mixture 1:2) against grasses in post-emergence application

|  | Compound A 30 g a.i./ha | Cyanazine 60 g a.i./ha | Compound A + Cyanazine 30 + 60 g a.i./ha | |
|---|---|---|---|---|
| weed species | % control | | WE | W |
| Alopecurus myosuroides | 82 | 10 | 84 | 97 |
| Lolium perenne | 45 | 22 | 57 | 83 |
| Setaria viridis | 62 | 55 | 83 | 95 |

Expected control of Alopecurus myosuroides, Lolium perenne and Setaria viridis was 84, 57 and 83 respectively, clearly demonstrating that the combination was synergistic.

Example 4 C

Herbicidal performance of the mixture Compound A+Cyanazine (60 g a.i./ha+120 g a.i./ha=mixture 1:2)

against Lolium perenne in post-emergence application

| weed species | Compound A 60 g a.i./ha | Cyanazine 120 g a.i./ha | Compound A + Cyanazine 60 + 120 g a.i./ha | |
|---|---|---|---|---|
| | % control | | WE | W |
| Lolium perenne | 47 | 55 | 76 | 95 |

Expected control of Lolium perenne was 76, clearly demonstrating that the combination was synergistic.

Example 4 D

Herbicidal performance of the mixture Compound A+Cyanazine (15 g a.i./ha+60 g a.i./ha=mixture 1:4) against grasses in post-emergence application

| weed species | Compound A 15 g a.i./ha | Cyanazine 60 g a.i./ha | Compound A + Cyanazine 15 + 60 g a.i./ha | |
|---|---|---|---|---|
| | % control | | WE | W |
| Alopecurus myosuroides | 60 | 10 | 64 | 80 |
| Apera spicaventi | 72 | 75 | 93 | 100 |
| Lolium perenne | 25 | 22 | 42 | 60 |
| Setaria viridis | 55 | 55 | 80 | 96 |

Expected control of Alopecurus myosuroides, Apera spica-venti, Lolium perenne and Setaria viridis was 64, 93, 42 and 80 respectively, clearly demonstrating that the combination was synergistic.

Example 4 E

Herbicidal performance of the mixture Compound A+Cyanazine (30 g a.i./ha+120 g a.i./ha=mixture 1:4) against grasses and Galium aparine in post-emergence application

| weed species | Compound A 30 g a.i./ha | Cyanazine 120 g a.i./ha | Compound A + Cyanazine 30 + 120 g a.i./ha | |
|---|---|---|---|---|
| | % control | | WE | W |
| Alopecurus myosuroides | 82 | 45 | 90 | 100 |
| Galium aparine | 77 | 50 | 89 | 97 |
| Lolium perenne | 45 | 55 | 75 | 85 |

Expected control of Alopecurus myosuroides, Galium aparine and Lolium perenne was 90, 89 and 75 respectively, clearly demonstrating that the combination was synergistic.

Example 4 F

Herbicidal performance of the mixture Compound A+Cyanazine (15 g a.i./ha+120 g a.i./ha=mixture 1:8) against Alopecurus myosuroides in post-emergence application

| weed species | Compound A 15 g a.i./ha | Cyanazine 120 g a.i./ha | Compound A + Cyanazine 15 + 120 g a.i./ha | |
|---|---|---|---|---|
| | % control | | WE | W |
| Alopecurus myosuroides | 60 | 45 | 78 | 92 |

Expected control of Alopecurus myosuroides was 78, clearly demonstrating that the combination was synergistic.

Example 5 A

Herbicidal performance of the mixture Compound A+Amidosulfuron (15 g a.i./ha+7.5 g a.i./ha mixture 2:1) against Galium aparine in post-emergence application

| weed species | Compound A 15 g a.i./ha | Amidosulfuron 7,5 g a.i./ha | Compound A + Amidosulfuron 15 + 7,5 g a.i./ha | |
|---|---|---|---|---|
| | % control | | WE | W |
| Galium aparine | 60 | 65 | 86 | 93 |

Expected control of Galium aparine was 86, clearly demonstrating that the combination was synergistic.

What is claimed is:

1. A herbicidal composition comprising a herbicidally acceptable carrier and/or surface active agent and, as active ingredient, a synergistically effective amount of at least one 2,6-disubstituted 4-methyl pyridine of formula I $$\text{(I)}$$

in which

X represents independently a halogen atom or a haloalkyl group; and n represents an integer of 1, 2 or 3, and at least one additional herbicidal compound, which is active against broad-leaved weeds and/or annual grasses, said additional herbicidal compound being selected from the group consisting of (a) a urea-type herbicide, (b) a triazine-type herbicide, (c) a sulfonylurea-type herbicide, and (d) a thiadiazole oxvacetamide herbicide.

2. A herbicidal composition according to claim 1 comprising a compound of formula 1, wherein X represents a fluoro atom and n is 1 or 2.

3. A herbicidal composition according to claim 2 wherein the compound of formula I is 2-(3,4-difluorophenoxy)-4-methyl-6-(1-methyl-3-trifluoromethylpyrazol-5-yl)-pyridine.

4. A composition as claimed in claim 1 wherein said additional herbicidal compound is selected from the group consisting of chlortoluron, isoproturon, cyanazine, amidosulfuron, and fluthiamide.

5. A composition as claimed in claim 1 wherein the ratio (by weight) of the 2,6-disubstituted 4-methyl pyridine to the additional herbicidal compound is from 10:1 to 1:200.

6. A composition as claimed in claim 5 wherein the ratio (by weight) is from 1:1 to 1:80.

7. A method of combating Alopecurus myosuroides, Lolium perenne, Setaria viridis, Stellaria media, Veronica persica, Galium aparine, Apera spica-venti and/or Lamium purpureum at a locus which comprises applying to the locus a herbicidally effective amount of a composition described in claim 1.

8. A method of controlling the growth of weeds at a locus which comprises applying to the locus a synergistically effective amount of both a compound of formula I and an additional herbicidal compound as defined in claim 1.

9. A method according to claim 8, wherein said compounds are applied together in a single formulation.

10. A method according to claim 8, wherein said compounds are applied in separate formulations.

11. A method for controlling the growth of weeds in cereal crops which comprises applying thereto a herbicidally effective amount of a composition according to claim 1.

* * * * *